(12) United States Patent
Forbrich (10) Patent No.: US 11,445,913 B2
(45) Date of Patent: Sep. 20, 2022

(54) PHOTOACOUSTIC ELECTROCARDIOGRAM-GATED KILOHERTZ VISUALIZATION

(71) Applicant: FUJIFILM Sonosite, Inc., Bothell, WA (US)

(72) Inventor: Alexander Erich Forbrich, Toronto (CA)

(73) Assignee: FUJIFILM Sonosite, Inc., Bothell, WA (US)

( * ) Notice: Subject to any disclaimer, the term of this patent is extended or adjusted under 35 U.S.C. 154(b) by 481 days.

(21) Appl. No.: 16/698,520

(22) Filed: Nov. 27, 2019

(65) Prior Publication Data
US 2020/0170511 A1    Jun. 4, 2020

Related U.S. Application Data

(60) Provisional application No. 62/775,113, filed on Dec. 4, 2018.

(51) Int. Cl.
*A61B 5/0205* (2006.01)
*A61B 5/0456* (2006.01)
*A61B 5/00* (2006.01)
*A61B 5/352* (2021.01)

(52) U.S. Cl.
CPC .......... *A61B 5/0044* (2013.01); *A61B 5/0205* (2013.01); *A61B 5/352* (2021.01); *A61B 2503/40* (2013.01); *A61B 2503/42* (2013.01)

(58) Field of Classification Search
CPC ..... A61B 5/0095; A61B 5/318; A61B 5/0044; A61B 5/0035; A61B 5/0205; A61B 8/4483; A61B 8/5284; A61B 5/352; A61B 5/113; G01N 21/1702; G01S 15/89
See application file for complete search history.

(56) References Cited

U.S. PATENT DOCUMENTS

| | | | |
|---|---|---|---|
| 7,052,460 | B2 | 5/2006 | Liu et al. |
| 7,674,228 | B2 | 3/2010 | Williams et al. |
| 7,798,963 | B2 | 9/2010 | White et al. |
| 2014/0198606 | A1 | 7/2014 | Morscher et al. |
| 2016/0051148 | A1 | 2/2016 | Sato |
| 2016/0310083 | A1 | 10/2016 | Wang et al. |

FOREIGN PATENT DOCUMENTS

WO    WO 2017/100920 A1    6/2017

OTHER PUBLICATIONS

International Search Report and Written Opinion dated Mar. 11, 2020 in International Application No. PCT/US2019/063565.

*Primary Examiner* — Jon Eric C Morales
(74) *Attorney, Agent, or Firm* — Baker Botts L.L.P.

(57) ABSTRACT

In one embodiment, a photoacoustic imaging system receives user input to specify one or more imaging wavelengths, and a target number of image frames to be taken of a target tissue region. The specified imaging wavelengths are set to capture at least two different photoabsorbing molecules in the target tissue. The photoacoustic imaging system takes image frames at the specified wavelengths, while the system also receives ECG and respiration data of the subject. Image frames are discarded based on the respiration data, and the other image frames are sorted into a plurality of slots corresponding to different points of the cardiac cycle from the ECG data. The system creates a composite image from the one or more wavelengths to show the target tissue of interest through the different points of the cardiac cycle.

6 Claims, 6 Drawing Sheets

PHOTOACOUSTIC ELECTROCARDIOGRAM-GATED KILOHERTZ VISUALIZATION

CROSS-REFERENCE TO RELATED APPLICATION(S)

The present application is related to, and claims the benefit of, U.S. Patent Provisional Application Ser. No. 62/775,113 filed Dec. 4, 2018, which is herein incorporated by reference in its entirety.

TECHNICAL FIELD

The disclosed technology relates to ultrasound imaging systems and in particular to simulated high-frame rate multispectral photoacoustic imaging.

BACKGROUND

High-frequency ultrasound imaging is a valuable tool for assessing small animal models of cardiovascular disease. However, there remain some limitations to functional assessment of the myocardium, since most measurements are based on mechanical properties of the muscle. Photoacoustic (PA) imaging is a hybrid optical and ultrasound imaging modality that uses pulsed laser light to visualize blood and measure oxygen saturation (sO2) levels. In addition, the ability to illuminate with multiple wavelengths (i.e. multispectral imaging) allows for the identification and quantification of different optical absorbers. For example, because oxy- and deoxyhemoglobin absorb light differently at different wavelengths, multispectral imaging may be used to quantify oxygen saturation within tissue—a useful physiological parameter in medical science research.

One limitation of this modality may be that the imaging frame rate is restricted by the pulse repetition frequency of the laser used to generate the photoacoustic signal. For example, on some current commercial photoacoustic systems, the frame rate may reach a maximum of 20 Hz for a single wavelength. In addition, if multispectral imaging is performed, the frame rate may be further reduced by a factor of the number of wavelengths being acquired and tissue motion may become even more of a problem because frames must be perfectly co-registered (frames at different wavelengths at the exact same spatial position) in order for proper quantification of the multispectral photoacoustic data to be performed.

This limitation may be especially evident in imaging rapidly moving organs such as the heart in small animal or laboratory animal research. For example, a mouse heart beats at a rate of 400-600 bpm (approx. 7 to 10 Hz), and imaging rates of hundreds of frames per second may be required to properly analyze every part of the cardiac cycle.

One method to address this issue may be to use higher frame rate laser systems. Although these types of laser systems do exist, these systems typically sacrifice the energy of each pulse in order to achieve the higher repetition rate or are prohibitively expensive. Sacrificing energy of the pulses may limit the achievable imaging depth and may prevent the visualization of the entire myocardium.

Even with high repetition rate lasers (50-100 Hz), the maximum temporal resolution may not be sufficient to properly quantify the signal over the entire cardiac cycle, as at least two wavelengths are required to measure oxygen saturation—a valuable measure in the cardiac muscle. At a frame rate of 50 Hz (which includes two wavelengths), fewer than 10 frames per heartbeat may be achieved which is not sufficient to analyze the dynamic changes in the myocardium that occur within every cardiac cycle. Also and perhaps more importantly, the time it takes to acquire two different wavelengths may be too long to be able to appropriately co-register the images acquired. In other words, by the time the frame for the second wavelength is acquired, the heart may have changed position and the two frames will not match up leading to spurious data.

An alternative approach to using high frame rate imaging may be to heavily average the frames acquired over many cardiac cycles which essentially "blurs" the image and the data alike leading to far less accurate measurements and a lack of sensitivity to small changes. It may also preclude any functional analysis of differing parts of the cardiac cycle, leading to a simple global estimate of oxygen saturation in the myocardium which is less useful and robust.

DETAILED DESCRIPTION

As will be explained in further detail below, the disclosed technology relates to improvements in ultrasound imaging systems and in particular to a multispectral photoacoustic imaging system that acquires and retrospectively processes imaging data to simulate a frame rate in excess of what is currently available on existing photoacoustic systems. Such a system is called "Photoacoustic ECG-gated kilohertz visualization." As the name implies, in particular embodiments, the target tissue may be imaged at an effective frame rate in excess of 1000 Hz, which may be sufficient to depict a continuously smooth image of the target tissue through movements such as a cardiac cycle, despite the actual imaging system only being capable of a frame rate on the order of 20 Hz.

Electrocardiography (or "ECG", and sometimes referred to as "EKG") refers to a technique used to monitor electrical signals originating from the heart during its movement. Electrical signals originating from the heart may be detected at the surface of the skin in the vicinity of the heart. The ECG signal may be used to track the cycle of heart function. Various "ECG gating" or "ECG synchronization" techniques have been developed to improve ultrasound image acquisition by making use of simultaneously acquired ECG signals to coordinate timing of image acquisition relative to the cardiac cycle. Previous imaging systems using ECG-gated processing have been described, for example, in U.S. Pat. No. 7,052,460, filed 15 Dec. 2003; U.S. Pat. No.

7,798,963, filed 3 Mar. 2006; and U.S. Pat. No. 7,674,228, filed 28 Feb. 2005, all of which are incorporated by reference herein.

In particular embodiments, a photoacoustic imaging system utilizes non-ionizing laser pulses that are directed into biological tissue. Some of the delivered energy may be absorbed by the tissue and converted into heat, generating ultrasonic emissions due to transient thermoelastic expansion. The ultrasonic emissions may then be detected by ultrasonic transducers for imaging. In particular embodiments, the strength of the ultrasonic emissions may be proportional to the local energy deposition, which may be related to the absorption of the laser pulses in the local region. In particular embodiments, the absorption spectra of one or more molecules in the local region may affect the ultrasonic emissions. As an example and not by way of limitation, two different wavelengths of laser pulses may be used to detect the concentration of oxyhemoglobin and deoxyhemoglobin in tissue. An example photoacoustic imaging system is the Vevo LAZR system from Fujifilm VisualSonics Inc.

In particular embodiments, a photoacoustic imaging system may allow a user to specify the number of target image frames to be captured, and the wavelengths to be sued. As an example and not by way of limitation, an animal heart may be imaged to analyze the oxygen saturation levels of the myocardium of the heart. In this example, the user may specify that 100 target image frames should be captured within a single cardiac cycle. The user may also specify that two wavelengths should be used for the photoacoustic imaging: one suitable for detecting deoxyhemoglobin, and a second suitable for detecting oxyhemoglobin. After the user has provided input, the photoacoustic imaging system may start capturing images at a first of the selected wavelengths. While the images are captured, the system may also receive ECG data and respiration data from leads placed on the subject. As an example and not by way of limitation, sets of leads may be placed on a mouse to detect ECG signals, and measure changes in resistivity which may indicate the phases of respiration over time.

In particular embodiments, the frame rate of the photoacoustic imaging system may be in the same order of magnitude as the cyclic rate of the target tissue. As an example and not by way of limitation, a photoacoustic imaging system may be capable of imaging at 20 Hz, while a mouse heart beats at approximately 7-10 Hz. In particular embodiments, the frame rate of the system may be optimized by reducing the total image area to be captured. As an example and not by way of limitation, an ultrasound transducer may include 256 elements, and 64 channels. In order to optimize the frame rate, only 64 elements may be used to capture the image. By taking numerous images of the target tissue, the photoacoustic imaging system may capture enough images so that at least one image of the target tissue at each phase of the cardiac cycle is captured. As an example and not by way of limitation, if the cardiac cycle according to the ECG data is divided into 100 frames, the photoacoustic imaging system may continue to image the heart at 20 Hz over several hundred images.

In particular embodiments, as the one or more image frames are received by the photoacoustic imaging system, the system may determine whether each image frame should be kept for creation of the composite image. In particular embodiments, the image frame may be discarded if the respiration data indicates that the subject is inhaling or exhaling, which may shift the location of the target tissue such as the heart. For image frames captured while the target tissue is moving, these image frames may be determined to be unsuitable for the composite image. If the respiration data confirms that the image frame should be kept, then based on the ECG data, the photoacoustic imaging system may determine where in the cardiac cycle the image frame should be placed. As an example and not by way of limitation, the photoacoustic imaging system may create 100 slots corresponding to 100 different points in time within a single cardiac cycle. Upon receiving the image frame, the photoacoustic imaging system may place the image frame within one of the 100 slots. In particular embodiments, the photoacoustic imaging system may continue taking additional image frames, until all 100 slots have been filled. In particular embodiments, before all of the slots are filled with image frames, two or more image frames may be assigned to the same slot. In such a case, the photoacoustic imaging system may combine the two or more image frames to create a single image frame representing that slot, which may improve the signal-to-noise ratio for the combined image frame compared to the individual image frames. Once all of the slots are filled, the photoacoustic imaging system may repeat the process with the next wavelength specified by the user. Once all the frame slots at all of the selected wavelengths have been filled, the photoacoustic imaging system may create a composite set of images depicting the absorption of the different wavelengths over a single cardiac cycle. In particular embodiments, the composite set of images may comprise a video that shows the absorption over the cardiac cycle. In particular embodiments, the compositing may be based on a processing mode specified by the user. As an example and not by way of limitation, the user may specify that the processing should be to detect oxygenated and deoxygenated tissue, or to process two or more specific molecules.

Figure 1:
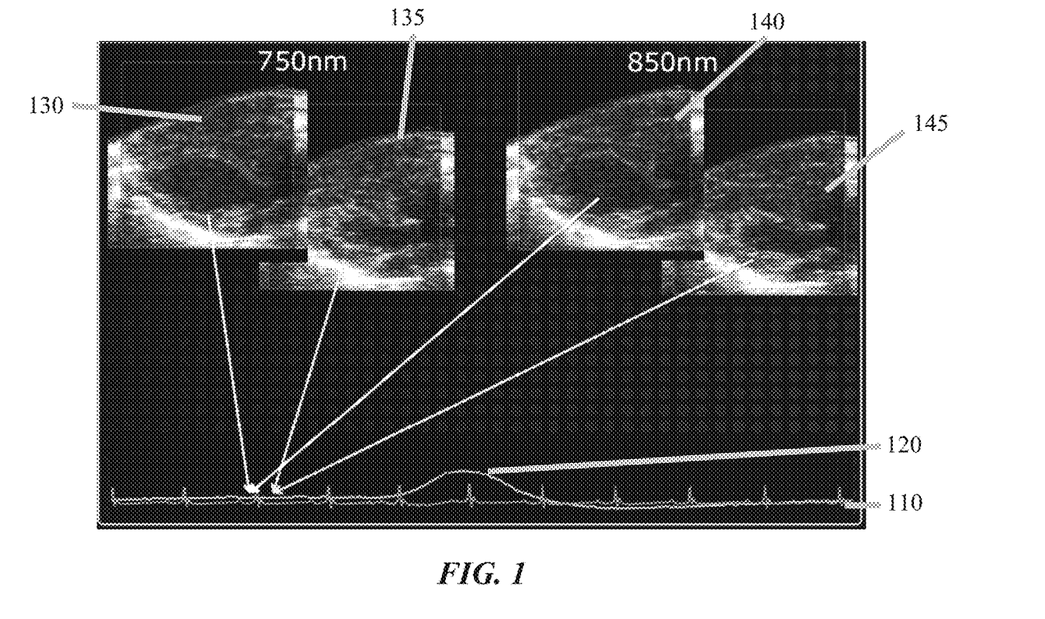
FIG. 1 depicts example photoacoustic images taken of a mouse heart at 750 nm and 850 nm, at two different points of the cardiac cycle.

FIG. 1 depicts an example set of photoacoustic images captured during two phases of a cardiac cycle. ECG data 110 is collected by leads placed on the subject, and respiration data 120 is collected by leads placed on the subject over the same period of time. In particular embodiments, the respiration data is based on a measurement of the resistivity across the body of the subject, which may change as the subject inhales and exhales. In the example of FIG. 1, the photoacoustic imaging system may capture a number of images at 750 nm and at 850 nm, for oxyhemoglobin and deoxyhemoglobin, respectively. Images 130 and 135 are photoacoustic images taken at 750 nm; images 140 and 145 are photoacoustic images taken at 850 nm. In the example of FIG. 1, the photoacoustic imaging system may determine that images 130 and 140 correspond to a first point on the ECG data 110, while images 135 and 145 correspond to a second point on the ECG data 110. For images 130, 135, 140, and 145, the photoacoustic imaging system may determine that the respiration data 120 confirms that the subject is not shifting during the first and second points on the ECG data 110. In the example of FIG. 1, the photoacoustic imaging system may then create a composite image such that images 130 and 140 are overlaid with each other, while images 135 and 145 are overlaid with each other. As an example and not by way of limitation, if images 130 and 135 were determined to be in adjacent slots for the cardiac cycle, and images 140 and 145 were determined to be in adjacent slots, the final composite image may depict the overlay of images 130 and 140, immediately followed by the overlay of images 135 and 145.

Figure 2:
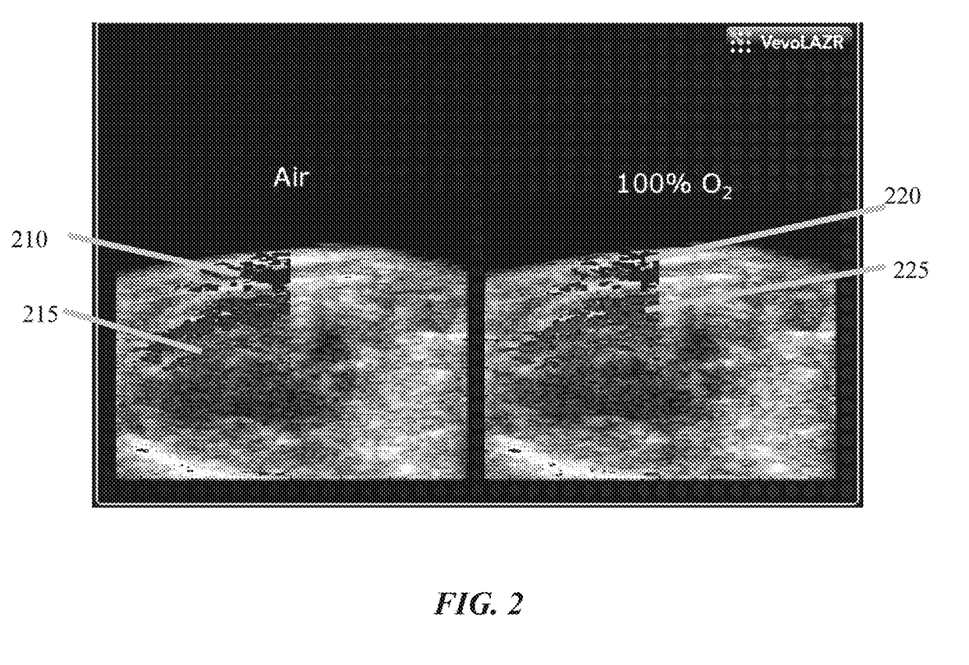
FIG. 2 depicts an example set of images showing two different molecules of interest in the target tissue through photoacoustic imaging.

FIG. 2 depicts two example composite frames at similar phases of the cardiac cycle. On the left side of FIG. 2, the subject has inspired laboratory air containing 20% oxygen, while on the right, the subject has inspired 100% oxygen. Regions 210 and 220 depict low-oxygenated tissue containing deoxyhemoglobin, while regions 215 and 225 depict high-oxygenated tissue containing oxyhemoglobin.

Figure 3A:
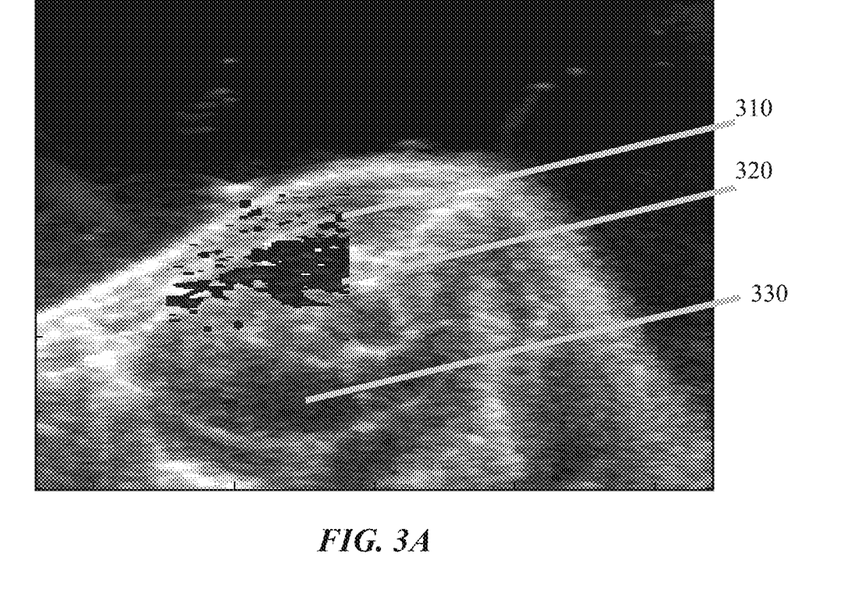
FIGS. 3A-3C depict an example set of images showing deoxyhemoglobin and oxyhemoglobin within the myocardium for an animal model respiring air with 20% oxygen.
Figure 3B:
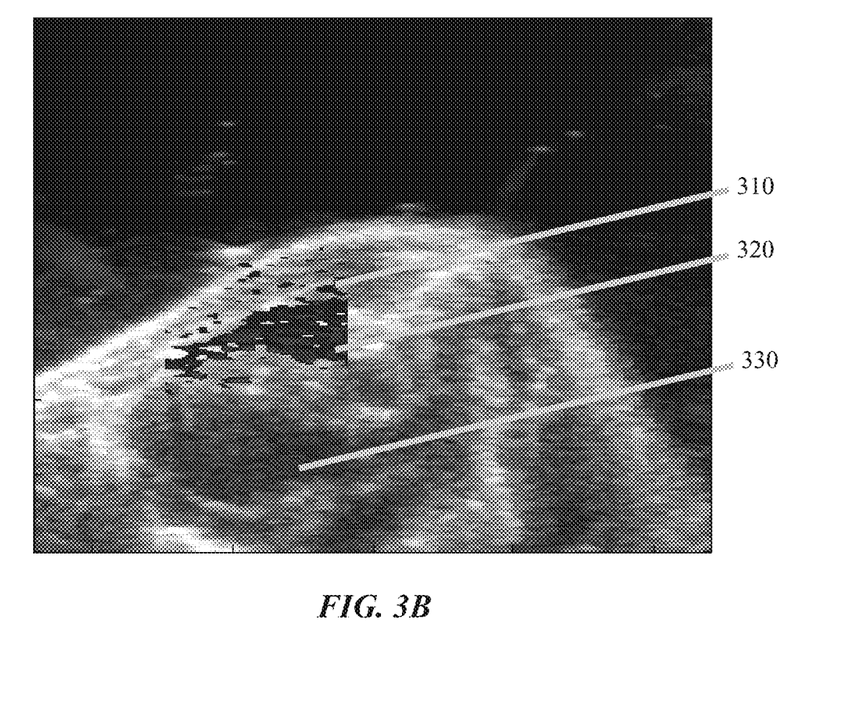
Figure 3C:
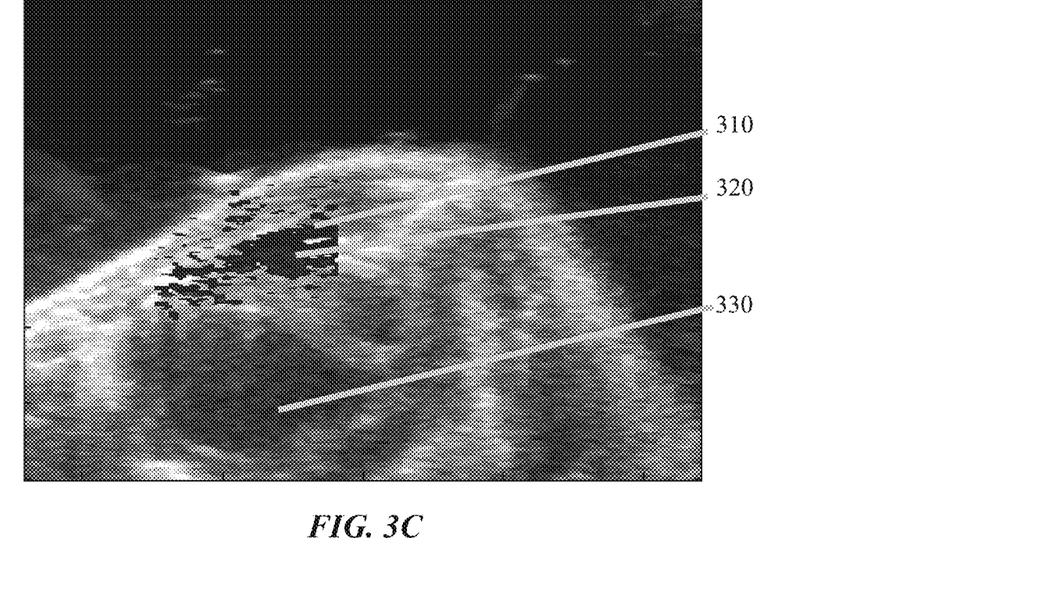

FIGS. 3A-3C depict composite frames at different phases of the cardiac cycle, for a subject exposed to laboratory air containing 20% oxygen. At the three phases depicted in FIGS. 3A-3C, the heart tissue 330 is visibly changing in size and shape over the cardiac cycle. Similarly, at each phase in FIGS. 3A-3C, deoxyhemoglobin is depicted by region 310, while oxyhemoglobin is depicted by region 320.

Figure 4A:
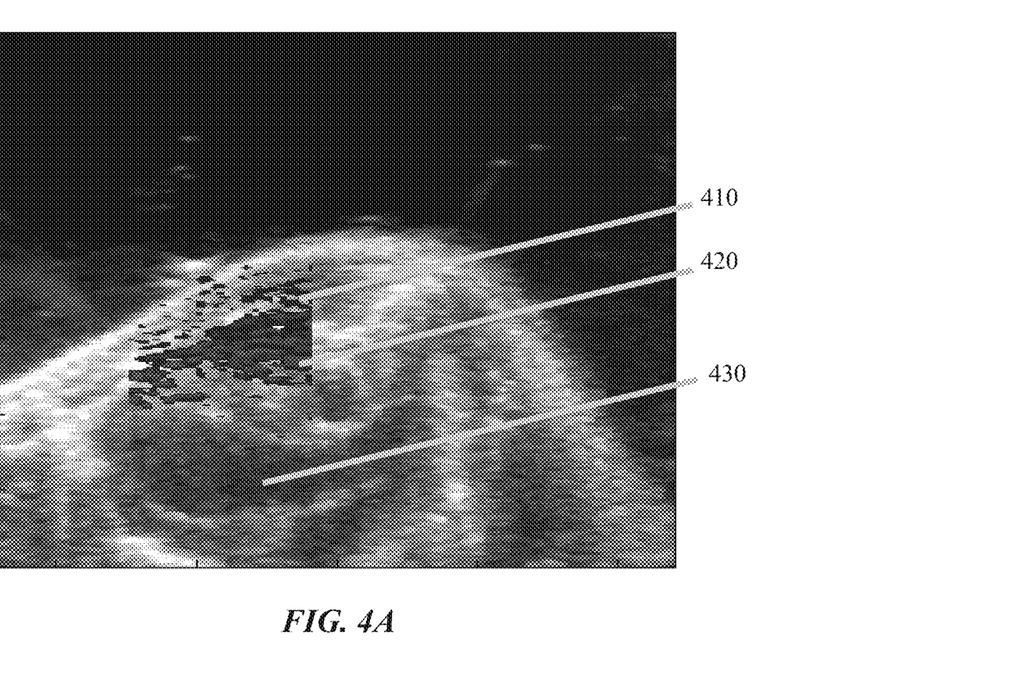
FIGS. 4A-4C depict an example set of images showing deoxyhemoglobin and oxyhemoglobin within the myocardium for an animal model respiring 100% oxygen.
Figure 4B:
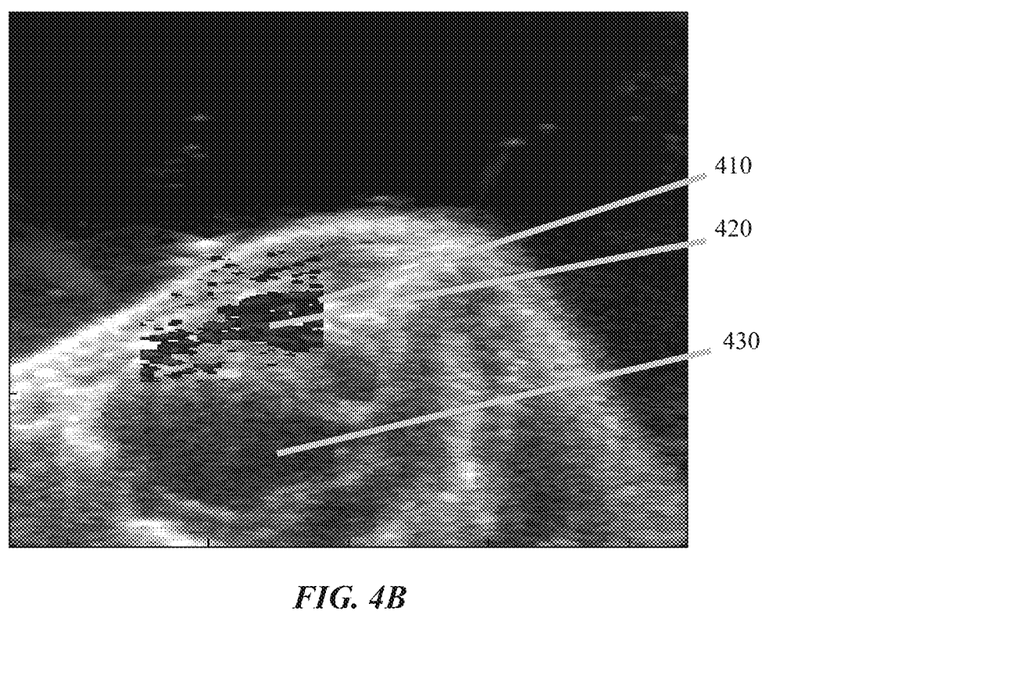
Figure 4C:
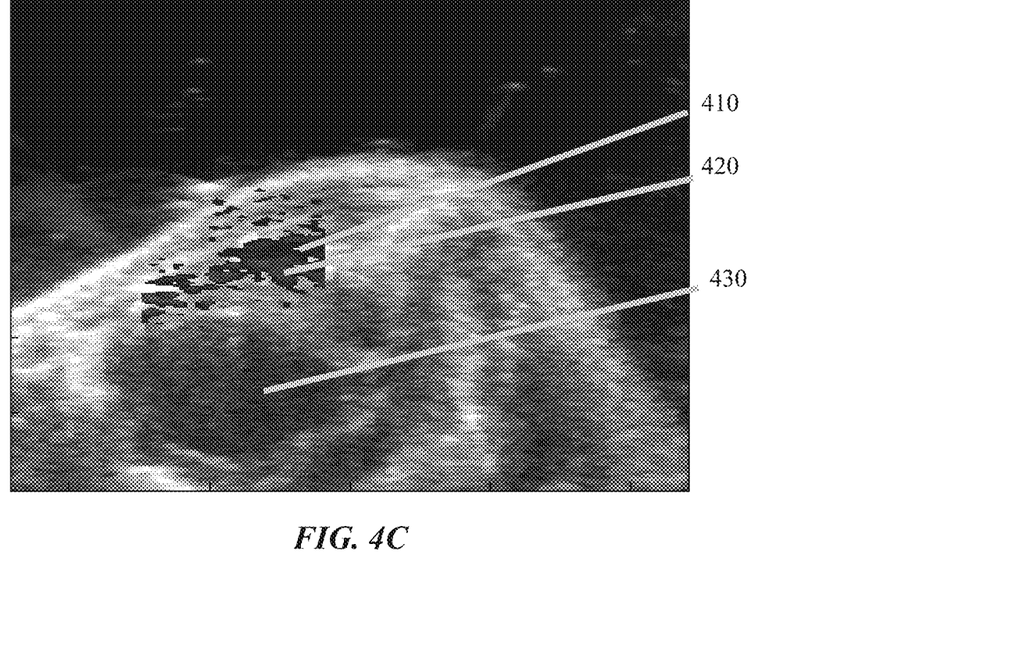

FIGS. 4A-4C depict composite frames at different phases of the cardiac cycle, for a subject exposed to 100% oxygen. At the three phases depicted in FIGS. 4A-4C, the heart tissue 430 is visibly changing in size and shape over the cardiac cycle. Similarly, at each phase in FIGS. 4A-4C, deoxyhemoglobin is depicted by region 410, while oxyhemoglobin is depicted by region 420.

In particular embodiments, the photoacoustic imaging system may conduct the following steps for ECG-gated kilohertz visualization of a subject animal:
1. The animal is placed on the animal imaging platform and hooked up to leads which collect and record ECG and respiration data.
2. The imaging window is set so that the maximum possible frame rate can be achieved while still covering the entirety of the heart.
3. Single wavelength photoacoustic data is performed at 750 nm wavelength until a set number of frames have been acquired. The number of frames should be sufficient to have at least a one frame of data for each point in the entire cardiac cycle when it is divided up into 100 discrete points.
4. Similar to the above step, single wavelength photoacoustic data is performed at 850 nm wavelength until a set number of frames have been acquired as per above.
5. For each wavelength, the acquired frames are then processed retrospectively to remove aberrant frames (due to respiration and animal movement as per the acquired respiration signal) and to rearrange and combine images according to where they fall during the cardiac cycle as per the acquired ECG signal.
6. Once at least one frame of each wavelength has been binned and the entirety of the cardiac cycle is complete with these two frames, a calculation of sO2 is performed according to the existing functionality of Oxy-Hemo mode on the system. The resulting parametric map of sO2 for one complete cardiac cycle is displayed and subsequent measurements can be performed as per the existing functionality of the system software.

In particular embodiments, for cardiac applications it may be possible to extend the concept to other parts of the cardiac system, for instance it may be useful to apply the technique to study blood vessels, valves and other fast moving activity directly related to the cardiac cycle.

In particular embodiments, the photoacoustic imaging system may use any number of wavelengths. As an example and not by way of limitation, additional wavelengths may be acquired and retrospectively processed to enable analysis of dyes, nanoparticles, fat, oxyhemoglobin, and/or deoxyhemoglobins. In particular embodiments, the tradeoff with including additional wavelengths may be to increase the total time required for image acquisition, as each additional wavelength would require sufficient time to capture a full set of images for that wavelength. As an example and not by way of limitation, current photoacoustic imaging systems may include existing software to spectrally separate the different components once the data has been processed as described above.

In particular embodiments, the photoacoustic imaging system may capture a 3D scan of the target tissue using the same retrospective processing. As an example and not by way of limitation, a linear motor may move the transducer through a series of positions (i.e. "slices") along the animal. At each slice, a 'PA EKV' image may be acquired as described above. In particular embodiments, the images may be reconstructed and visualized as a 3D render through time.

In particular embodiments, a potential drawback of the multispectral process described above may be that the data acquisition may take approximately one minute per wavelength. In particular embodiments, a quality option can enable users to select how many discrete points are used to cover the entire cardiac cycle. As an example and not by way of limitation, by reducing the number of cardiac phases to be imaged to 30 frames rather than 100, the total amount of time necessary for capturing the composite image may be reduced by a factor of about three, at the cost of reducing the frame rate for each cardiac cycle, which may render the composite video less smooth.

Figure 5:
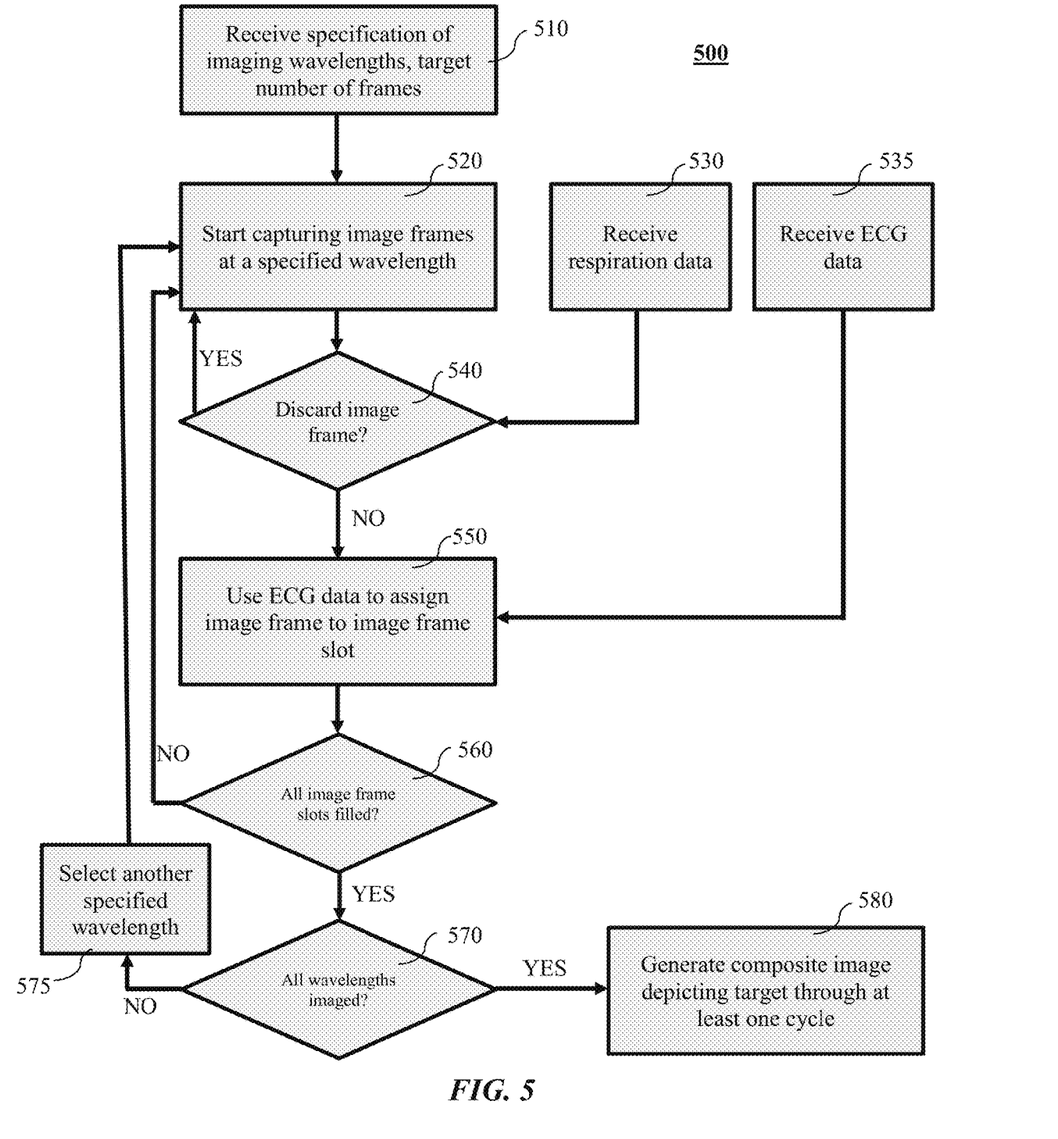
FIG. 5 depicts an example method of performing photoacoustic ECG-gated kilohertz visualization of a target tissue region.

FIG. 5 depicts an example method 500 of performing a photoacoustic ECG-gated kilohertz visualization process according to the teachings of the foregoing. The method 500 starts at step 510, where the photoacoustic imaging system may receive user input specifying the number of imaging wavelengths to be used and the wavelengths, and the number of target image frames to be captured. As an example and not by way of limitation, the user may specify that two wavelengths at 750 nm and 850 nm should be used, and 100 frames should be captured to depict a cardiac cycle. At step 520, the photoacoustic imaging system may start capturing image frames using one of the specified wavelengths. In this example, the system may start capturing 750 nm photoacoustic images. While step 520 is occurring, at steps 530 and 535, the photoacoustic imaging system receives concurrent ECG and respiration data for the subject. Each image frame captured at step 520 may be associated with an ECG state and a respiration state corresponding to the state of the subject at the time the image frame was captured. At step 540, the photoacoustic imaging system may determine, based on the corresponding respiration data, whether the particular image frame should be kept, or discarded. If the image frame is discarded, the photoacoustic imaging system returns to step 520 to continue capturing additional image frames at the same wavelength. If the image frame is kept, then at step 550, the photoacoustic imaging system uses the ECG data to assign the image frame to one of the image frame slots to be used for creating the composite image. In particular embodiments, the number of image frame slots may be equal to the target number of frames specified by the user at step 510. At step 560, the photoacoustic imaging system determines whether all image frame slots for the specified wavelength have been filled. If no, then the process returns to step 520 to continue capturing more image frames. If yes, then the system determines at step 570 whether all specified wavelengths have been filled. If no, then at step 575, the photoacoustic imaging system selects another specified wavelength, and repeats the process from step 520 at the new wavelength. If yes, then at step 580, the system generates a composite image depicting the target tissue through at least one cardiac cycle, showing the images captured at each specified wavelength.

Particular embodiments may repeat one or more steps disclosed in FIG. 5, where appropriate. Although this disclosure describes and illustrates particular steps of the method of FIG. 5 as occurring in a particular order, this disclosure contemplates any suitable steps of the method of FIG. 5 occurring in any suitable order. Moreover, although this disclosure describes and illustrates particular components, devices, or systems carrying out particular steps of the method of FIG. 5, this disclosure contemplates any suitable combination of any suitable components, devices, or systems carrying out any suitable steps of the method of FIG. 5.

The subject matter and the operations described in this specification may be implemented in digital electronic circuitry, or in computer software, firmware, or hardware, including the structures disclosed in this specification and their structural equivalents, or in combinations of one or more of them. Embodiments of the subject matter described in this specification may be implemented as one or more computer programs, i.e., one or more modules of computer program instructions, encoded on computer storage medium for execution by, or to control the operation of, data processing apparatus.

A computer storage medium may be, or may be included in, a computer-readable storage device, a computer-readable storage substrate, a random or serial access memory array or device, or a combination of one or more of them. Moreover, while a computer storage medium is not a propagated signal, a computer storage medium may be a source or destination of computer program instructions encoded in an artificially-generated propagated signal. The computer storage medium also may be, or may be included in, one or more separate physical components or media (e.g., multiple CDs, disks, or other storage devices).

The term "processor" encompasses all kinds of apparatus, devices, and machines for processing data, including by way of example a programmable processor, a computer, a system on a chip, or multiple ones, or combinations, of the foregoing. The apparatus may include special purpose logic circuitry, e.g., an FPGA (field programmable gate array) or an ASIC (application-specific integrated circuit). The apparatus also may include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment may realize various different computing model infrastructures, such as web services, distributed computing and grid computing infrastructures.

A computer program (also known as a program, software, software application, script, or code) may be written in any form of programming language, including compiled or interpreted languages, declarative or procedural languages, and it may be deployed in any form, including as a stand-alone program or as a module, component, subroutine, object, or other unit suitable for use in a computing environment. A computer program may, but need not, correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program may be deployed to be executed on one computer or on multiple computers that are located at one site or distributed across multiple sites and interconnected by a communication network.

The processes and logic flows described in this specification may be performed by one or more programmable processors executing one or more computer programs to perform actions by operating on input data and generating output. The processes and logic flows may also be performed by, and apparatus can also be implemented as, special purpose logic circuitry, e.g., an FPGA (field programmable gate array) or an ASIC (application-specific integrated circuit).

Processors suitable for the execution of a computer program may include, by way of example and not by way of limitation, both general and special purpose microprocessors. Devices suitable for storing computer program instructions and data may include all forms of non-volatile memory, media and memory devices, including by way of example but not by way of limitation, semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory may be supplemented by, or incorporated in, special purpose logic circuitry.

From the foregoing, it may be appreciated that specific embodiments of the invention have been described herein for purposes of illustration, but that various modifications may be made without deviating from the scope of the invention.

What is claimed is:

1. A photoacoustic imaging system comprising an image processor configured to:
   receive user input specifying:
      one or more imaging wavelengths; and
      a target number of image frames to be taken of a target tissue region;
   for each of the one or more specified imaging wavelengths:
      capture an image frame to be taken at the specified imaging wavelength;
      while the image frame is captured, receive electrocardiography (ECG) data and respiration data associated with the target tissue region;
      determine, based on the respiration data, whether to discard the image frame;
      in response to determining that the image frame should not be discarded, assigning, based on the ECG data, the image frame to one of a plurality of image frame slots, wherein:
         the plurality of image frame slots is equal to the target number of image frames; and
         each image frame slot corresponds to a different point on a cardiac cycle determined from the ECG data;
      continuing to capture additional image frames until at least one image frame has been assigned to each image frame slot in the plurality of image frame slots;
   in response to determining that at least the target number of image frames have been captured at each of the specified imaging wavelengths, combining the image frames from the one or more imaging wavelengths to create a composite image frame depicting the target tissue through at least one cardiac cycle.

2. The system of claim 1, wherein each of the one or more imaging wavelengths is intended for a specific optically-absorbing molecule.

3. The system of claim 1, wherein the respiration data comprises a measurement of the resistivity across a body of the subject comprising the target tissue.

4. The system of claim 1, wherein determining whether to discard the image frame based on the respiration data comprises determining that the target tissue has shifted in position, and discarding the image frame.

5. The system of claim 1, further comprising:
- determining that two or more image frames are assigned to a single image frame slot for a specified imaging wavelength; and
- combining the two or more image frames to create a single composite image frame assigned to the single image frame slot.

6. The system of claim 1, wherein the combining the image frames from the one or more imaging wavelengths to create a composite image frame is done through a process selected by a user input.

* * * * *